United States Patent [19]

Chapman

[11] 3,966,417

[45] June 29, 1976

[54] APPARATUS FOR CONTACTING ALKYLATE CONTAINING ALKYL FLUORIDE WITH HYDROGEN FLUORIDE

[75] Inventor: Charles C. Chapman, Bartlesville, Okla.

[73] Assignee: Phillips Petroleum Company, Bartlesville, Okla.

[22] Filed: Sept. 13, 1973

[21] Appl. No.: 397,028

Related U.S. Application Data

[62] Division of Ser. No. 159,884, July 6, 1971, Pat. No. 3,784,628.

[52] U.S. Cl. .............................. 23/283; 23/288 E; 260/683.48
[51] Int. Cl.² .......................... B01J 1/00; B01J 8/08; C07C 3/54
[58] Field of Search .......... 23/284, 283, 285, 288 E; 260/683.48; 208/213

[56] References Cited
UNITED STATES PATENTS

| | | |
|---|---|---|
| 2,165,490 | 7/1939 | Kranz.............................. 23/283 X |
| 3,499,734 | 3/1970 | Newman et al....................... 23/283 |
| 3,598,542 | 8/1971 | Carson et al....................... 23/284 X |

Primary Examiner—Morris O. Wolk
Assistant Examiner—Arnold Turk

[57] ABSTRACT

An apparatus comprising a substantially upright vessel having the following sections: a lower acid from hydrocarbon alkylate effluent settling section, an intermediate section containing a riser conduit equipped with contacting elements, perforate disks which may be spaced apart or other means, and an upper settling section having means for introducing high purity HF therein for downflow through said riser countercurrently to the upflowing alkylate, means for removing settled alkylate from said upper settling section, and means for removing acid containing alkyl fluorides from said lower settling section.

5 Claims, 1 Drawing Figure

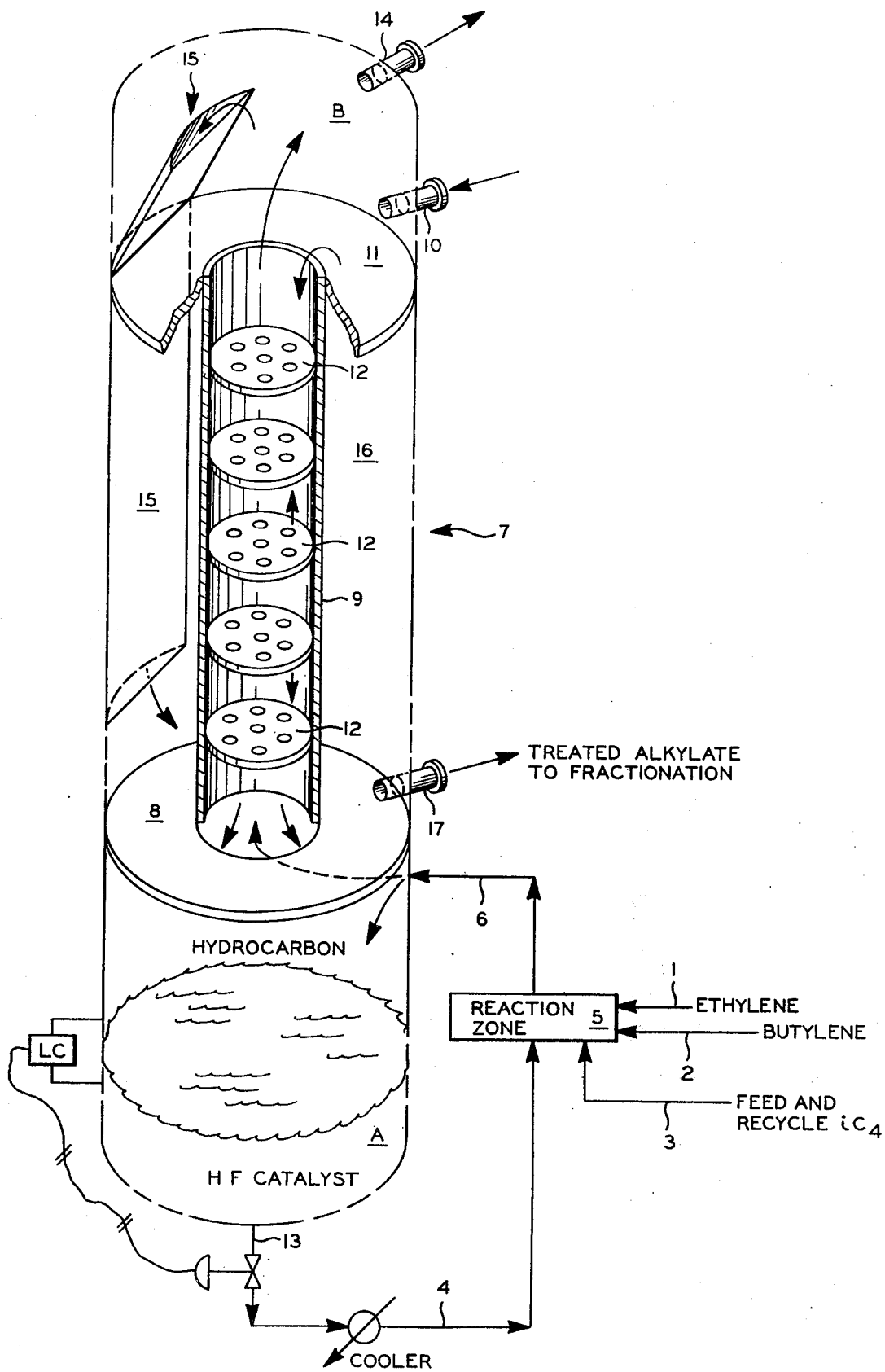

APPARATUS FOR CONTACTING ALKYLATE CONTAINING ALKYL FLUORIDE WITH HYDROGEN FLUORIDE

This is a division of application Ser. No. 159,884, filed July 6, 1971, now U.S. Pat. No. 3,784,628, issued Jan. 8, 1974.

This invention relates to alkylation of hydrocarbons. In one of its aspects it relates to the alkylation of an isoparaffin with an olefin under conditions forming alkyl fluoride. In a more specific aspect the invention relates to an apparatus for removing alkyl fluoride from an alkylate.

In one of its concepts the invention provides an apparatus for effecting a method for contacting or recontacting hydrocarbon alkylate effluent with high strength acid in a unitary operation comprising a lower settling zone, an intermediate contacting zone, and an upper settling zone, the alkylation effluent containing alkyl fluoride being passed to said lower settling zone and allowed to settle acid therefrom therein, the hydrocarbon being passed upwardly through said contacting zone in countercurrent flow to high strength or purity HF acid flowing down through said contacting zone, the alkylate effluent having been thus contacted being collected in an upper settling zone and removed therefrom. In one of its concepts the alkylate from the upper settling zone is passed as a separate stream to an intermediate zone surrounding said contacting zone and thence to fractionation. More specifically in a further concept the invention provides an apparatus comprising a substantially upright vessel having the following sections: a lower acid from hydrocarbon alkylate effluent settling section, an intermediate section containing a riser conduit equipped with contacting elements, perforate disks which may be spaced apart or other means, and an upper settling section having means for introducing high purity HF therein for downflow through said riser countercurrently to the upflowing alkylate, means for removing settled alkylate from said upper settling section, and means for removing acid containing alkyl fluorides from said lower settling section.

In a combination operation employing the apparatus of the invention the acid now containing alkyl fluoride is returned to the alkylation operation and/or for rerun or other treatment which can include addition thereto of additional isoparaffin and olefin, including a higher olefin, for production of additional alkylate.

In Ser. No. 138,991 filed Apr. 30, 1971 and now U.S. Pat. No. 3,761,540, which is a continuation-in-part of Ser. No. 79,405, filed Oct. 12, 1970 and now abandoned, there is described and claimed a process for the alkylation of an isoparaffin with ethylene in the presence of a higher olefin using hydrofluoric acid as a catalyst. Depending upon the conditions employed in that operation there will be varying amounts or no alkyl fluoride in the alkylate obtained.

It is desirable to recover the alkyl fluoride and to beneficiate the same by converting it to additional alkylate.

Various apparatus and method steps have been proposed.

In my copending application Ser. No. 139,017, filed Apr. 30, 1971 and now U.S. Pat. No. 3,763,264, I have described a method for converting alkyl fluoride in an alkylate to additional alkylate by contacting the same with an isoparaffin using additional HF acid which comprises the steps of introducing the alkyl fluoride containing alkylate into a lower section of an alkylate treating zone, in said zone passing alkylate upwardly into a midsection of said zone through a zone for subdividing said alkylate (which has isoparaffin such as isobutane therein) and then into an upwardly extended riser-reaction zone while introducing additional HF acid to the alkylate as it emerges from said alkylate subdividing zone and passes upwardly into said riser-reaction zone.

The method of that application also comprises passing reacted alkylate and acid upwardly to an upper section of said treating zone, permitting acid and hydrocarbons to settle out forming a lower acid phase and an upper hydrocarbon phase, removing the upper hydrocarbon phase, returning settled acid phase downwardly surrounding said riser-reaction zone to said alkylate subdividing zone for admixture of the acid with the subdivided alkylate as it emerges from said subdividing zone. Still further in that application, the method comprises passing a portion of acid from the upper settling section of said treating zone downwardly to the lower section of said treating zone with a head sufficient so as to permit pumping the raw alkylate into said lower zone and to pass the same forcefully upwardly through said alkylate subdividing zone into contact with acid therein.

The present invention differs from the invention of the said application in that in the present invention there is countercurrent flow of the high purity acid with the hydrocarbons in the alkylate. Thus, the high purity acid is introduced to the top of the riser contacting element. Further, the contacting elements or perforate disks or equivalent of the present invention are disposed throughout a substantial length of the contacting zone or riser element. Other differences and distinctions are evident from a consideration of this disclosure and the drawing.

An object of this invention is to provide an apparatus for the alkylation of hydrocarbons. A further object of the invention is to provide for the removal of alkyl fluoride formed during the alkylation of hydrocarbons from an alkylate containing the same. A still further object of the invention is to provide apparatus to recover and convert alkyl fluoride formed during the alkylation of hydrocarbons employing hydrofluoric acid. A still further object of the invention is to provide a unitary apparatus for recovering alkyl fluoride from alkylation effluent.

Other aspects, concepts and the several advantages of the invention are apparent from a study of this disclosure, the drawing and the appended claims.

According to the present invention there is provided an apparatus for effecting a method which comprises alkylating an isoparaffin, e.g., isobutane and/or isopentane, with, say, ethylene, and a higher olefine, e.g., propylene or a butylene, in the presence of hydrofluoric acid, passing an alkylation effluent thus obtained into an alkyl fluoride recovery operation comprising in a unitary zone a lower settling section, separating a substantial portion of acid from the alkylation effluent in such section, passing alkylate hydrocarbon thus obtained upwardly through an extended contacting section countercurrently to high purity HF acid descending therethrough, and thence to an upper settling section and from said settling section to fractionation. In one embodiment the method passes thus treated hydrocarbon separately downwardly from the last mentioned settling section into an intermediate section surrounding said contacting section and thence to fractionation.

Thus according to the invention there is provided an apparatus consisting essentially of a unitary shell divided into three sections, a lower section having an inlet and an outlet and at its top being closed by a plate extending across said shell, said plate having mounted thereon a riser conduit, an opening in said plate permitting communication between the bottom section and said riser conduit, said riser conduit containing contacting elements which can be spaced apart and terminating at its upper end below the top of said shell, another plate extending across said shell at the end of said conduit, said conduit being in open communication through a perforation in said plate with the uppermost portion of said shell, means for introducing a fluid into the upper portion of said shell for downflow through said riser conduit, and means for removing fluid from the top of said shell.

Referring now to the drawing, ethylene, butylene and isobutane are fed together with HF through conduits 1,2,3 and 4 into reactor 5 under alkylation conditions to produce an alkylation effluent removed at 6.

The conditions of alkylation, the mole ratios, temperature pressure and other reaction conditions such as the presence or absence of boron trifluoride are set forth in U.S. Pat. No. 3,761,540. These conditions do not form a part of the present invention.

The alkylation effluent in 6 enters vessel 7 in its lower section A. In section A, acid settles from the hydrocarbon and hydrocarbon is passed upwardly through the opening in plate 8 into riser conduit 9 wherein it contacts downwardly flowing acid introduced at 10 and passing downwardly through plate 11 into riser conduit 9. Spaced apart perforate disks 12 placed transverse to the axis of the riser conduit insure good contacting and recovery of alkyl fluoride in the alkylation effluent hydrocarbon. This fluoride is taken with the downflowing acid into the lower portion of section A and ultimately by 13 back to reactor 5. Thus, the hydrocarbon passes upwardly into section B above plate 11. In section B any acid remaining in the hydrocarbon settles and substantially acid-free hydrocarbon, which may contain some acid, is removed from section B by pipe 14. As a feature of the invention, a downcomer pipe 15 takes hydrocarbon effluent from the top of section B downwardly into a midsection of the vessel 16. This hydrocarbon fraction assists in cooling the riser reactor and therefore to dissipate the heat of absorption of the ethyl fluoride in the hydrofluoric acid. Hydrocarbon is removed to fractionation by conventional means through pipe 17.

The following is a specific example of operation according to the present invention. This example is based upon knowledge of the art and engineering calculations.

SPECIFIC EXAMPLE

| | |
|---|---|
| Reactor (5): | |
| Temperature, °F. | 90 |
| Pressure | To Maintain Liquid Phase |
| (1) Ethylene, B/D | 700 |
| (2) Butylenes, B/D | 300 |
| (3) Feed and Recycle Isobutane, B/D | 13,450 |
| (4) HF Catalyst, B/D | 58,000 |
| | |
| Hydrocarbon from (A) into (9): | |
| Flow, B/D | 14,140 |
| Volume Percent: | |
| Normal Butane and Lighter | 89 |
| $C_5$ plus (Alkylate) | 11 |
| Organic Fluorides, ppm by wt. | 16,000 |
| | |
| High Purity HF (10) into (9): | |
| Flow, B/D | 400 |
| Wt. % HF | 98 |
| Organic Fluorides, ppm by wt. | 1,000 |
| | |
| Temperature in Zone 9, °F. | 90 |
| | |
| Hydrocarbon from (14) and/or (17): | |
| Flow, B/D | 13,820 |
| Volume Percent: | |
| Normal Butane and Lighter | 88.5 |
| $C_5$ plus (Alkylate) | 11.5 |
| Organic Fluorides, ppm by wt. | 1,600 |
| | |
| Zone 16: | |
| Height, ft. | 16 |
| Diameter, ft. | 6.5 |
| | |
| Contactor 9: | |
| Height, ft. | 16 |
| Diameter, ft. | 1 |
| Plates 12, number | 8 |
| Area of Orifices, Each Orifice, sq. in. | 0.5 |
| Number of Orifices per Plate | 360 |

Additional alkylate produced from the organic fluorides recovered amounts to 140 barrels per day, valued at $900.

Reasonable variation and modification are possible within the scope of the foregoing disclosure, drawings and the appended claims to the invention the essence of which is that there has been set forth an apparatus for recovering from an alkylation hydrocarbon effluent alkyl fluoride by contacting said alkylate effluent containing said alkyl fluoride to remove alkyl fluoride therefrom by contacting the same in a unitary vessel comprising three sections, a lower, intermediate and an upper section, effluent being passed from the lower section through a riser conduit in the intermediate section into a top section while high purity acid is passed in the top section for downflow through the riser conduit and ultimately down into the bottom section and from there to alkylation, hydrocarbon thus treated being passed from the top of the vessel to fractionation; in a more specific form the riser conduit containing at least one mixing and contacting element.

I claim:

1. An apparatus for the contacting of two liquids which comprises a unitary vessel containing a lower section, an intermediate section, and an upper section, the upper portion of said lower section being delineated by a plate extending across the vessel, a means in the upper portion of said lower section for introducing a liquid into said lower section, a means in the lower portion of said lower section for withdrawing a liquid from said lower section, an upright riser conduit mounted on said plate in cooperation with a perforation in said plate to permit liquids from said lower section to rise into said riser conduit, said plate being in fluidtight connection with the walls of said vessel and said riser conduit, said riser conduit containing mixing and contacting elements, said riser conduit extending upwardly from said plate a substantial distance along the vessel and defining with the vessel an annulus, a second plate having a perforation therein associated with said riser conduit to permit communication between the upper section and the lower section through said riser conduit, said second plate being in fluid-tight connection with the walls of said vessel and with the upper portion of said riser conduit, said second plate defining the upper portion of the intermediate section and the lower portion of said upper section means for introducing a liquid into said upper section at a lower portion thereof, and a downcomer conduit with one of its ends near the top of said vessel in said upper section, the other end of said downcomer conduit extending downwardly through said upper plate so that liquid in the top of said section can be passed downwardly through said downcomer into the annulus formed between the vessel and the riser conduit in the intermediate section of the vessel, and means provided for removing liquids in said annulus portion of the intermediate section from the vessel.

2. An apparatus according to claim 1 wherein the top portion of the upper section contains a means for removing liquid from the upper portion of the upper section in addition to the downcomer means.

3. An apparatus according to claim 1 wherein the mixing and contacting elements within the riser conduit comprises a plurality of spaced apart plates each containing a plurality of perforations, said plates being placed transverse to the axis of the riser conduit throughout the length of the riser conduit in engagement with the interior walls of said riser conduit.

4. An apparatus according to claim 3 wherein each plate in the riser conduit has several hundred perforations, with each perforation having an area of about 0.5 square inch.

5. An apparatus according to claim 4 wherein the vessel has a diameter of about 6.5 feet, the riser conduit a height of about 16 feet and a diameter of about 1 foot, and the perforations in the plates dividing the vessel into its three sections being about 1 foot in diameter.

* * * * *